Nov. 16, 1965 A. CHABERT Plant Pat. 2,573
ROSE PLANT
Filed Aug. 6, 1964
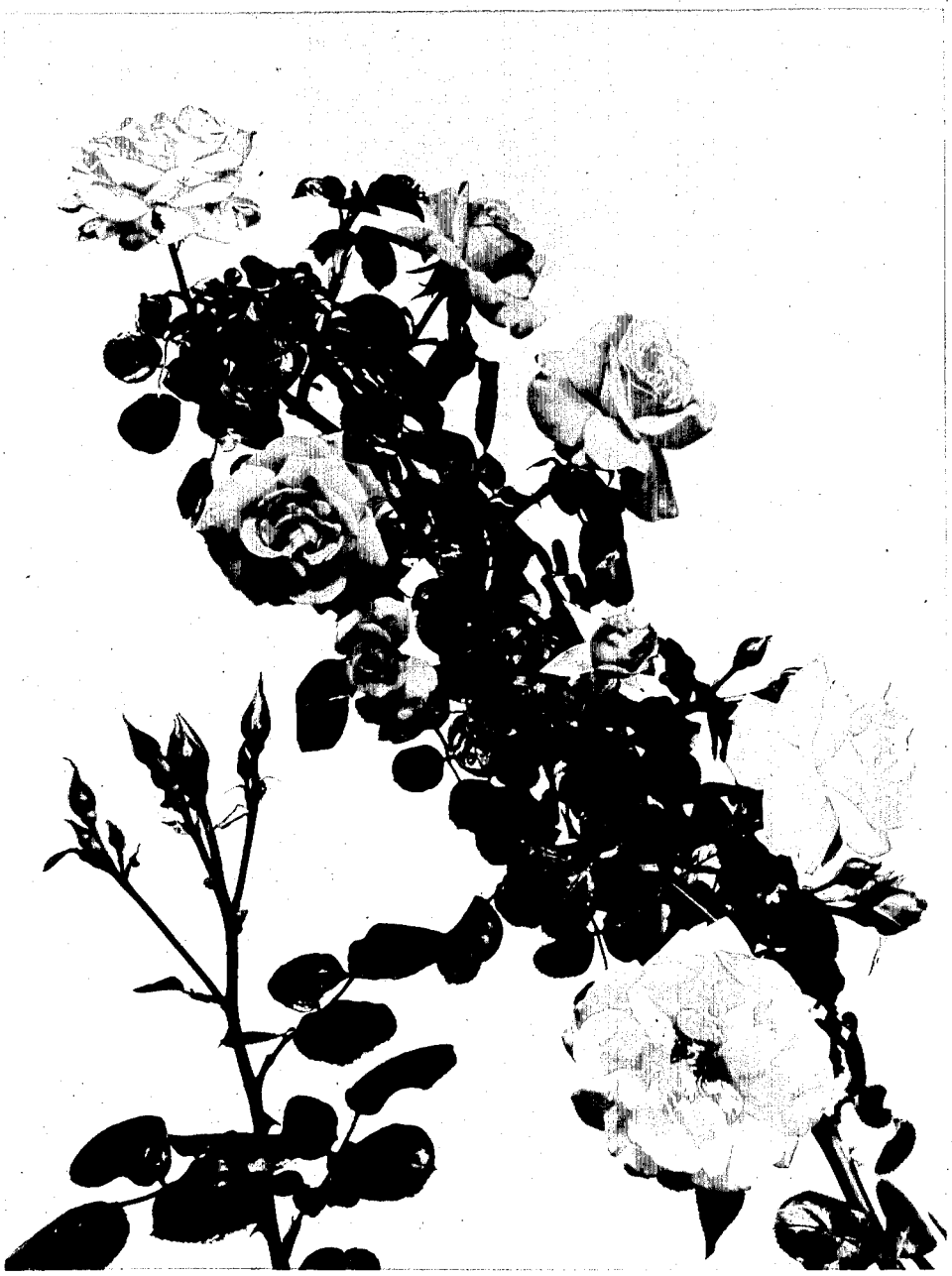
Inventor.
Andre Chabert
By: Robb & Robb
Attorneys.

United States Patent Office

Plant Pat. 2,573
Patented Nov. 16, 1965

2,573
ROSE PLANT

André Chabert, Paris, France, assignor, by mesne assignments, to Armstrong Nurseries, Inc., Ontario, Calif., a corporation of California Filed Aug. 6, 1964, Ser. No. 388,025
Claims priority, application France, Aug. 21, 1963, 43,940
1 Claim. (Cl. Plt.—6)

The present invention relates to a new and distinct variety of rose plant of the climber class, which was originated by me by crossing the variety known in the United States as "Spectacular" (U.S. Plant Patent No. 1,416) with an unnamed and unpatented seedling of "Rome Glory" (U.S. Plant Patent No. 304)×"La Vaudoise" (unpatented), the variety "Spectacular" being the seed parent, and the unnamed seedling being the pollen parent.

The primary objective of this breeding was to combine the ever-blooming climbing habit, floriferousness and orange-red color of the seed parent "Spectacular" with the non-fading flower characteristic and high quality foliage of the pollen parent. This objective was fully achieved, along with other desirable improvements, as evidenced by the following unique combination of characteristics which are outstanding in the new variety and which distinguish it from its parents, as well as from all other varieties of which I am aware:

(1) A vigorous, climbing plant habit, with ample disease-resistant, glossy foliage, which is reddish when young but which changes to a rich dark green color when mature;

(2) A relatively ever-blooming flowering habit, with heavy flowering in the spring and intermittent blooming thereafter throughout the remainder of the growing season;

(3) Excellent floriferousness, with double flowers of medium size borne both singly and in small clusters;

(4) A flower form which is above average, with high-centered, urn-shaped buds; and (5) A relatively non-fading bright, rich Scarlet to orange-red color of the flowers, which is the most outstanding characteristic of my new rose variety and which is unusual for a rose of the climbing class.

In comparison with its seed parent "Spectacular," the new variety has a bright, rich, relatively non-fading Scarlet or orange-red color which is always good when compared to the orange-red or Scarlet color of the flowers of "Spectacular," which tends to fade more and in some weather conditions tends to take on a dull cast in the case of the flowers of "Spectacular."

As compared with the unnamed pollen parent which bears flowers of a relatively non-fading bright Vermilion Red color, my new variety is differentiated therefrom by being a climber instead of a bush like this parent.

Asexual reproduction of my new variety by budding, as performed in France and also at Ontario, California, U.S.A., shows that the aforementioned characteristics and distinctions come true to form and are established and transmitted through succeeding propogations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "W") and Robert Ridgway's Color Standards and Nomenclature (hereinafter abbreviated as "R"), except where general color terms of ordinary dictionary significance are obvious:

Type: Climbing; outdoor; seedling; for cut flowers and for garden decoration.

Class: Climber.

Breeding: Seedling.

*Seed parent.*—"Spectacular."

*Pollen parent.*—An unnamed seedling of "Rome Glory"×"La Vaudoise."

Propagation: Holds its distinguishing characteristics through succeeding propagations by budding.

Where propagated: Ontario, California, U.S.A., and in France.

*Flower*

Locality where grown and observed: Ontario, California, U.S.A.

Flowers borne: Sometimes singly but sometimes from three to five or more to stem; in irregular clusters; on stems of medium length and normal strength.

Quantity of bloom: Abundant; outdoors.

Continuity: Intermittent; most flowers during April-June at Ontario, California.

Fragrance: From none to slight.

Bud:

*Peduncle.*—From short to average length; erect; usually smooth; with few to several small to medium size stipitate glands. Color—near Absinthe Green, Plate XXXI "R," side exposed to sun overlaid with near Ocher Red, Plate XXVII "R."

*Before calyx breaks.*—Size—from small to medium. Form—from short to medium length; ovoid.

*As calyx breaks.*—Color—near Currant Red, Plate 821, page 167 "W"; area exposed to sun longer near Pansy Purple, Plate 928, page 177 "W."

*Sepals.*—Inner surface—with fine, wooly tomentum. Margins of alternate sepals—lined with fine, wooly tomentum. Margins of others—with few to many small stipitate glands and small to medium size foliaceous appendages. Outer surface of sepals—usually with few to several small stipitate glands and few to many hairs.

*As first petal opens.*—Size—from small to average. Form—from short to medium length; between ovoid and urn-shaped. Color: outside—near Scarlet, Plate 19/1, page 19 "W," with areas exposed to sun longer near Pansy Purple, Plate 928/3, page 177 "W"; inside—near Scarlet, Plate 19, page 19 "W," with small area at base of petal near Sulphur Yellow, Plate 1/2, page 1 "W."

*Opening.*—Opens up well; is not retarded or prevented from opening by cold, hot, wet, or dry weather.

Bloom:

*Size (when open).*—Average; from 3¾ inches to 4½ inches.

*Petalage.*—Double; from 25 to 35 petals, plus 4 to 10 petaloids; arranged irregularly.

*Form.*—High-centered at first but becoming cupped to high-centered; petals at first being tightly cupped, with tips reflexed outward, but becoming later at maturity loosely flat to cupped with tips reflexed outward; outside and intermediate petals of both newly opened and three-days-open flowers usually reflexed outward both along edges and apex of petal; outside petals usually strongly reflexed outward.

Petals:

*Texture.*—Moderately leathery.

*Appearance.*—Inside—satiny. Outside—satiny.

*Shape.*—Outside—between round and broadly obovate, with apex flat, and usually with 1 or 2 notches.—Intermediate—obovate, with apex rounded to flat and sometimes with 1 or 2 notches. Inside—narrowly obovate, with apex rounded and sometimes with 1 or 2 notches.

This description of a newly opened flower was made from a rose grown outdoors during the month of May at Ontario, California, U.S.A.:

*Color.*—Outer petal: outside surface—near Geranium Lake, Plate 20, page 20 "W," with small area at base of petal near Uranium Green, Plate 63/1, page 63 "W"; inside surface—near Scarlet, Plate 19, page 19 "W," with small area at base of petal near Uranium Green, Plate 63/2, page 63 "W." Intermediate petal: outside surface—near Scarlet, Plate 19/1, page 19 "W," with small area at base of petal near Uranium Green, Plate 63/2, page 63 "W"; inside surface—between Vermilion, Plate 18, page 18 "W" and Scarlet, Plate 19, page 19 "W," with small area at base of petal near Uranium Green, Plate 63/2, page 63 "W." Inner petal: outside surface—near Scarlet, plate 19/1, page 19 "W," with small area at base of petal near Uranium Green, Plate 63/1, page 63 "W," sometimes with small whitened area from base toward apex; inner surface—near Vermilion, Plate 18, page 18 "W," with small area at base of petal near Uranium Green, Plate 63/2, page 63 "W," sometimes with small whitened area from base toward apex.

This description was made from a rose that was open for three days outdoors during the month of May at Ontario, California, U.S.A.:

*Color.*—Outer petal: outside surface—between Geranium Lake, Plate 20/1, page 20 "W" and Carmine, Plate 21/1, page 21 "W"; inside surface—between Scarlet, Plate 19/1, page 19 "W" and Geranium Lake, Plate 20/1, page 20 "W," with small area at base of petal near Primrose Yellow, Plate 601/2, page 65 "W." Inner petal: outside surface—near Geranium Lake, Plate 20/1, page 20 "W," sometimes with whitened area from base toward apex; inside surface—between Scarlet, Plate 19, page 19 "W" and Geranium Lake, Plate 20, page 20 "W," sometimes with small whitened area at apex.

*General color effect.*—Newly opened flower—between Vermilion, Plate 18, page 18 "W" and Scarlet, Plate 19, page 19 "W." Three-days open—between Scarlet, Plate 19/1, page 19 "W" and Geranium Lake, Plate 20, page 20 "W."

*Behavior.*—Drop off cleanly; not particularly affected by cold, hot, wet or dry weather.

*Flower longevity.*—On bush in garden—4 or 5 days in July. Cut roses grown outdoors and kept at living room temperatures—4 to 6 days in July.

*Reproductive organs*

Stamens: Average number; arranged regularly about pistils.

Filaments: From short to medium length; from 6 mm. to 12 mm. in length; most with anthers. Color—near Crimson, Plate 22/2, page 22 'W."

Anthers: Medium size; all open approximately at once. Color: Upper side—margins near Straw Yellow, Plate 604/1, page 67 "W"; with remainder near Fuchsine Pink, Plate 627/3, page 78 "W"; under side—margins near Straw Yellow, Plate 604/1, page 67 "W," with remainder near Fuchsine Pink, Plate 627/3, page 78 "W."

Pollen: From moderate to abundant. Color—near Cadmium Orange, Plate 8, page 8 "W."

Pistils: Average number; approximately 50 in number.

Styles: Moderately even; from short to average length; thin; bunched. Color—upper ⅓ to ½ of style near Scarlet, Plate 19/2, page 19 "W," with remainder near Empire Yellow, Plate 603/2, page 66 "W."

Stigma: Color—near Chrome Yellow, Plate 605/2, page 144 "W."

Ovaries: Usually all enclosed in calyx.

Hips: Average length; between obovoid and globular; smooth; walls thick and fleshy. Color (½ mature)—near Absinthe Green, Plate XXXI "R."

Sepals: Usually permanent; medium length; straight. Color: inside—near Vetiver Green, Plate XLVII "R"; outside—near Grape Green, Plate XLI "R."

Seeds: From few to average number; from 10 to 20 in number; medium size.

*Plant*

Foliage:

*Leaves.*—Compound of usually 3–7 leaflets; abundant; large; leathery; glossy.

*Leaflets.*—Shape—broadly oval, with apex acute. Base—round. Margin—simply serrate.

*Color.*—Mature: upper surface—near Dark Dull Yellow-Green, Plate XXXII "R"; under surface—near Light Elm Green, Plate XVII "R." Young: upper surface—between Jade Green, Plate XXXI "R" and Deep Olive, Plate XL "R"; under surface—near Olive-Green, Plate IV "R."

*Rachis (the supporting stem of the compound leaf).*—From average size to heavy. Upper side—grooved; few to several small stipitate glands on edges. Under side—smooth; with few stipitate glands and from none to few small prickles.

*Stipules.*—From medium length to long; medium width, with short points turning out at an angle of usually less than 45°.

*Disease resistance.*—Better than average resistance to mildew, as compared with other varieties grown under comparable cultural conditions at Ontario, California, U.S.A.

Growth:

*Habit.*—Climbing; much-branched.

*Growth.*—Vigorous.

*Canes.*—Heavy caliper.

*Main stems.*—Color—near Rainette Green, Plate XXXI "R." Large prickles—from several to many; medium length; hooked slightly downward; with medium length; moderately broad base; color—near Mikado Brown, Plate XXIX "R." Small prickles—from few to several; color—near Mikado Brown, Plate XXIX "R." Hairs—none.

*Branches.*—Color—near Lincoln Green, Plate XLI "R." Large prickles—from several to many; from medium length to long; hooked slightly downward; with long, narrow base; color—near Russet, Plate XV "R." Small prickles—from none to few. Color—near Russet, Plate XV "R." Hairs—none.

*New shoots.*—Color—near Absinthe Green, Plate XXXI "R," with side exposed to sun overlaid with near Chestnut-Brown, Plate XIV "R." Large prickles—few; from short to medium length; hooked slightly downward; with short, narrow base; color—near Neutral Red, Plate XXXVIII "R." Small prickles—from none to few; color—near Neutral Red, Plate XXXVIII "R." Hairs—none.

I claim:

A new and distinct variety of rose plant of the climber class, substantially as herein shown and described, characterized particularly as to novelty by the unique combination of a vigorous, climbing plant habit, with ample disease resistant, glossy foliage which is reddish when young but which changes to a rich dark green color when mature, a relatively ever-blooming flowering habit, with heavy flowering in the spring and intermittent blooming thereafter throughout the remainder of the growing season, excellent floriferousness, with double flowers of medium size borne both singly and in small clusters, a flower form which is above average, with high-centered, urn-shaped buds, and a relatively non-fading, bright, rich Scarlet to orange-red color of the flowers, which is the most outstanding characteristic of my new rose variety and which is unusual for a rose of the climbing class.

No references cited.

ABRAHAM G. STONE, *Primary Examiner.*